US006742289B2

(12) United States Patent
Celmo

(10) Patent No.: US 6,742,289 B2
(45) Date of Patent: Jun. 1, 2004

(54) STRESS REDUCTION KIT AND METHOD OF USING SAME

(75) Inventor: George D. Celmo, San Diego, CA (US)

(73) Assignee: Medical Device Group, Inc.

( * ) Notice: Subject to any disclaimer, the term of this patent is extended or adjusted under 35 U.S.C. 154(b) by 128 days.

(21) Appl. No.: 10/186,429

(22) Filed: Jul. 1, 2002

(65) Prior Publication Data

US 2004/0000076 A1 Jan. 1, 2004

(51) Int. Cl.[7] .................................................. A61F 5/14

(52) U.S. Cl. ................................ 36/141; 36/43; 36/44; 601/28

(58) Field of Search ............................ 36/140, 141, 43, 36/44, 1; 601/28

(56) References Cited

U.S. PATENT DOCUMENTS

| | | | | | |
|---|---|---|---|---|---|
| ,682,141 | A | | 9/1901 | Galloway | |
| 1,128,220 | A | | 2/1915 | Bullard | |
| 3,100,483 | A | | 8/1963 | Altmeger et al. | |
| 3,595,244 | A | | 7/1971 | Kugler | |
| 3,744,483 | A | | 7/1973 | Picolin | |
| 3,757,774 | A | | 9/1973 | Hatuno | |
| 3,885,555 | A | | 5/1975 | Nobbs | |
| 4,047,310 | A | * | 9/1977 | Sunoo | 36/11.5 |
| 4,329,981 | A | | 5/1982 | Dungl | |
| 4,598,484 | A | * | 7/1986 | Ma | 36/3 R |
| 4,712,539 | A | | 12/1987 | Kim | |
| 4,813,405 | A | | 3/1989 | Filip | |
| 4,841,647 | A | * | 6/1989 | Turucz | 36/44 |
| 4,841,648 | A | * | 6/1989 | Shaffer et al. | 36/43 |
| 4,852,553 | A | * | 8/1989 | Voykin | 601/28 |
| 4,934,071 | A | | 6/1990 | Virgini | |
| 5,096,188 | A | * | 3/1992 | Shen | 482/51 |
| 5,154,682 | A | * | 10/1992 | Kellerman | 36/44 |
| 5,167,225 | A | | 12/1992 | Cheng I | |
| 5,186,703 | A | * | 2/1993 | Huang | 482/148 |
| 5,493,791 | A | | 2/1996 | Kramer | |
| 5,551,173 | A | * | 9/1996 | Chambers | 36/44 |
| 5,682,690 | A | * | 11/1997 | Chang | 36/141 |
| 5,784,811 | A | * | 7/1998 | Mauch | 36/141 |
| 5,860,229 | A | | 1/1999 | Morgenstern | |
| 6,219,941 | B1 | | 4/2001 | Kukoff | |
| 6,315,786 | B1 | | 11/2001 | Smuckler | |
| 6,434,859 | B1 | | 8/2002 | Kim | |

* cited by examiner

*Primary Examiner*—M. D. Patterson
(74) *Attorney, Agent, or Firm*—Jerry R. Potts

(57) ABSTRACT

A stress reduction kit includes a display package holding a pair of perforated reflex pin holders each with a printed foot reflexology chart integrally formed thereon. To facilitate creating pressure points on the feet of a user, the stress reduction kit also includes a bag of reflex pins, where each pin is dimensioned to be received in a friction tight fit into any one of the perforations disposed in the reflex pin holders and a set of instructions that guide a user on the placement of individual ones of the reflex pins in respective ones of the reflex pin holders. In accordance with the method of the present invention, when the user inserts the reflex pins in selected ones of the perforations and places the reflex pin holders within his or her shoes, desired body responses are achieved relative to the pressure points created by the pins against the feet of the user.

28 Claims, 3 Drawing Sheets

STRESS REDUCTION KIT AND METHOD OF USING SAME

TECHNICAL FIELD

The present invention relates to a kit and method for helping to reduce stress and tension in individuals, both males and females, by the application of pressure points to selected areas on the feet of a user.

BACKGROUND

Stress and tension are leading factors in causing deteriorating health in individuals, both males and females. Therefore it would be highly desirable to have a new and improved stress reduction kit and method of using the kit to help restore and maintain a healthy balance in the mind and body of an individual by strengthening the body immune system.

SUMMARY OF THE INVENTION

A stress reduction kit includes a display package holding a pair of perforated reflex pin holders each with a printed foot reflexology chart integrally formed thereon. To facilitate creating pressure points on the feet of a user, the stress reduction kit also includes a bag of reflex pins, where each pin is dimensioned to be received in a friction tight fit into any one of the perforations disposed in the reflex pin holders and a set of instructions that guide a user on the placement of individual ones of the reflex pins in respective ones of the reflex pin holders. In accordance with the method of the present invention, when the user inserts the reflex pins in selected ones of the perforations and places the reflex pin holders within his or her shoes, desired body responses are achieved relative to the pressure points created by the pins against the feet of the user.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein:

FIG. 6 is a pictorial view of another right foot reflex pin holder of another stress reduction kit, which is constructed in accordance with the present invention; and.

BEST MODE FOR CARRYING OUT THE INVENTION

Figure 1:
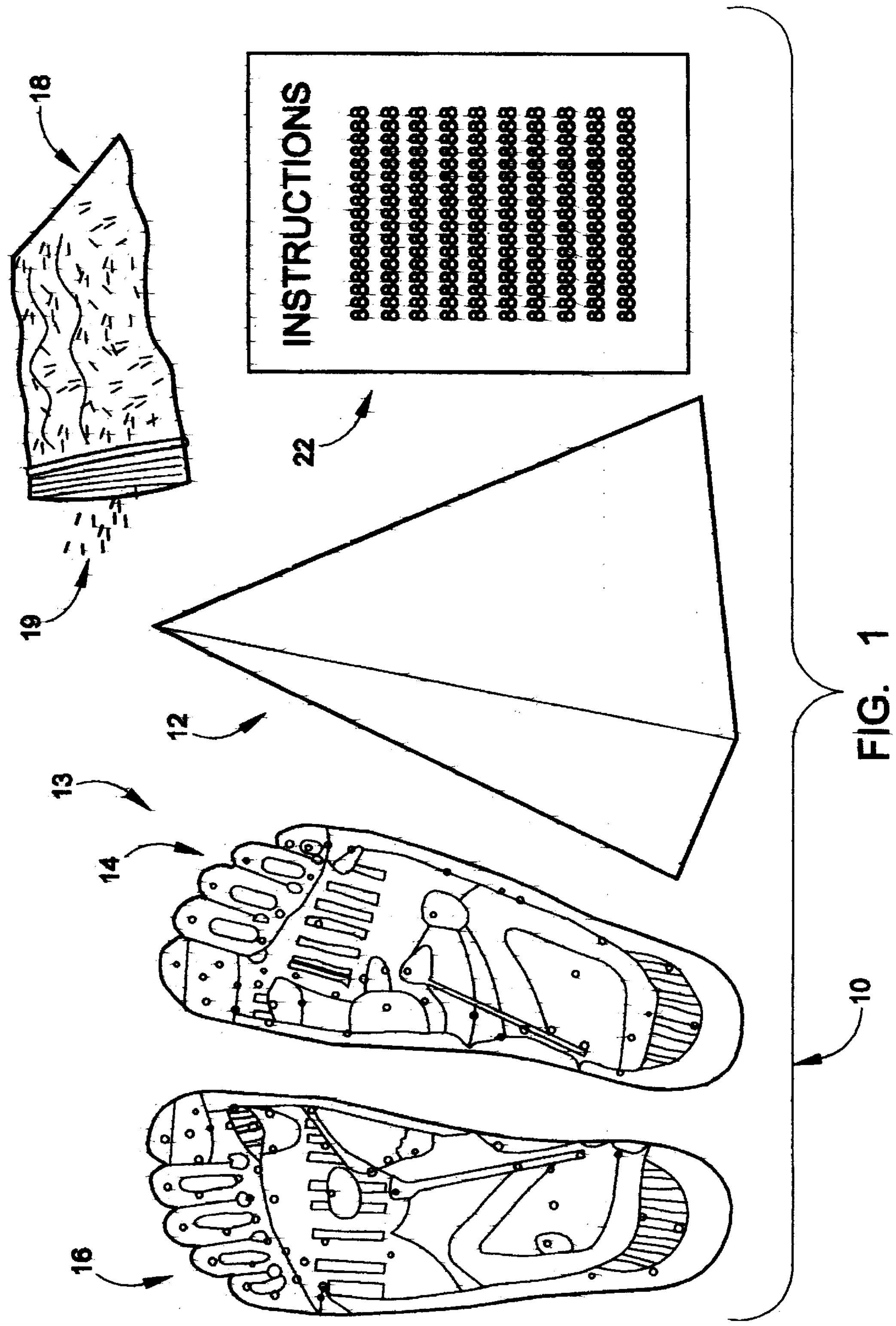
FIG. 1 is a pictorial view, illustrating operative elements of a stress reduction kit, which is constructed in accordance with the present invention.

Referring now to the drawings, and more particularly to FIG. 1 thereof, there is shown a stress reduction kit 10, which is constructed in accordance with the present invention. The kit 10 is used according to the method of the present invention to help relieve tension and stress, and it can be used in almost any location, and it is relatively inexpensive to manufacture.

Considering now the stress reduction kit 10 in greater detail with reference to FIGS. 1–5, the stress reduction kit 10 is conveniently packaged for display purposes in a pyramid shaped cardboard container 12 that has a sufficiently large interior to held the various remaining elements of the kit 10 which include: a pair 13 of perforated reflex pin holders consisting of a right foot reflex pin holder or right foot insole 14 and a left foot reflex pin holder or left foot insole 16, a resalable bag 18 holding a plurality of similar reflex pins or pressure pins 19, such as the pressure pin 20 (FIG. 4), and a set of instruction 22 that assist or guide a user relative to the placement of individual ones of the pressure pins in the reflex pin holders 14 and 16 respectively to achieve a desired effect on the body of the user. More particularly, in accordance with a stress reduction method of the present invention, when a user follows the instruction 22 by placing individual ones of the pressure pins, such as the pressure pin 20, in selected ones of the perforations provided in the insoles 14 and 16 respectively, the user will produce pressure points by engaging the pressure pins, such as the pressure pin 20, to create user desired pressure points on the body of the user as will be explained hereinafter in greater detail.

Figure 3:
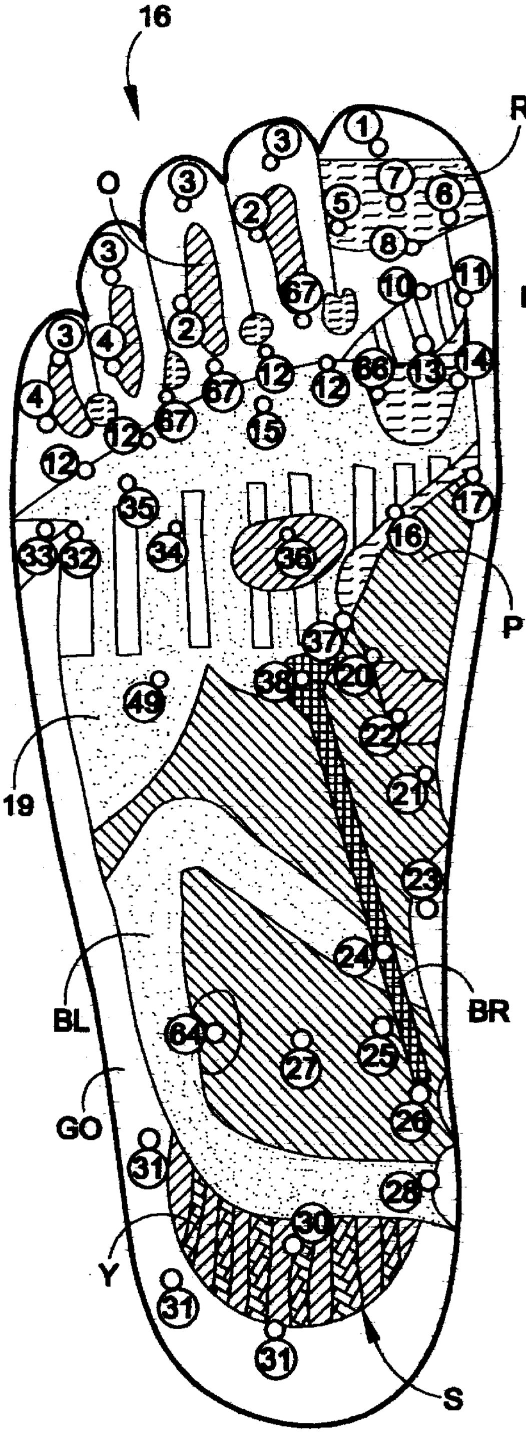
FIG. 3 is a pictorial view, of a left foot reflex pin holder of FIG. 1.
Figure 2:
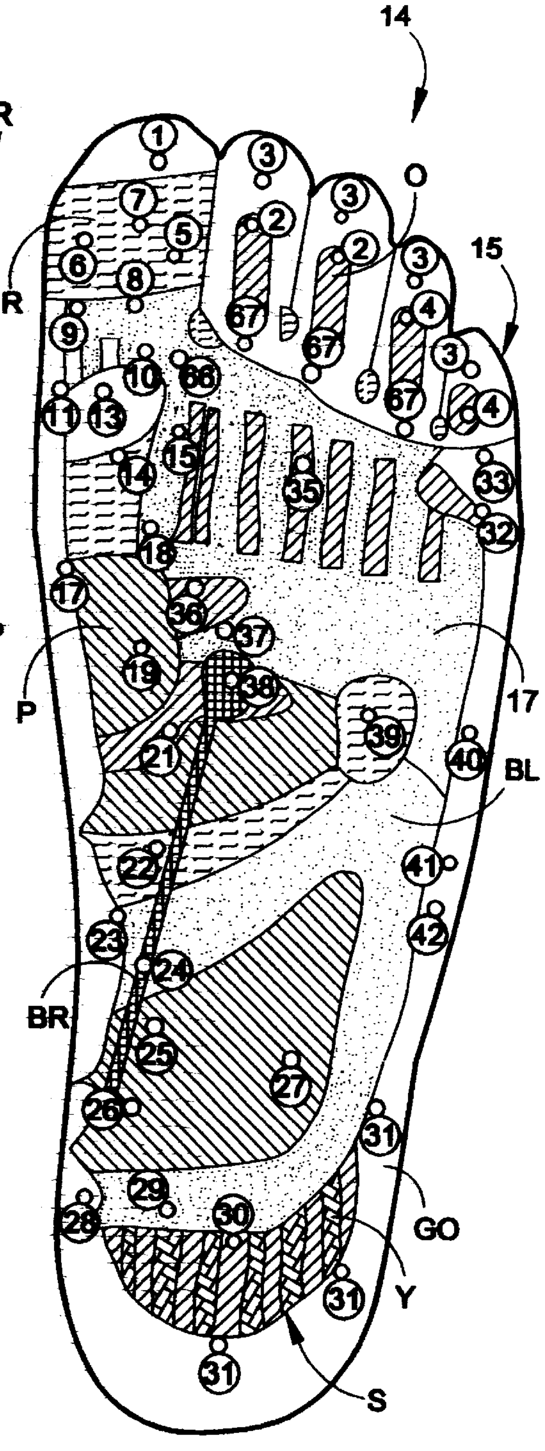
FIG. 2 is a pictorial view, of a right foot reflex pin holder of FIG. 1.

Considering now the reflex pin holders 14 and 16 in greater detail with reference to FIGS. 1–3, the reflex pin holders 14 and 16 are manufactured from a sponge like cellular material, such as a latex foam material 24, with a consistency ranging from flexible to substantially ridged with a high degree of resilience. The holders 14 and 16 are shaped to conform to the under portion of the anatomy of human feet so as to function as inner soles for the right and left shoes of the user. In this regard, the holders 14 and 16 are dimensioned for various shoe sizes and shoe widths.

Figure 5:
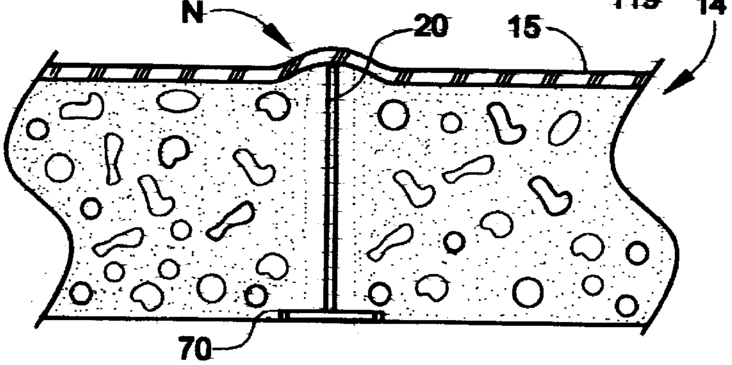
FIG. 5 is a cross sectional view taken substantially on line 5—5 of the right foot reflex pin holder of FIG. 2.

As best seen in FIG. 5, a thin sheet of plastic material is bonded to the top surface of each holder 14 and 16, such as plastic sheet 15. The undersurface of the plastic sheet 15 carries indicia in the form of reflexology chart 17 for the right foot. A different reflexology chart 19 is provided for the left foot as best seen in FIG. 3. In this regard, the indicia is color coded with yellow indica indicated generally at Y, with red indicia indicated generally at R, with blue indicia indicated generally at B, with brown indicia indicated generally at M, with purple indicia indicated generally at P, with orange indicia indicated generally at O, with gold indicia indicated generally at GO, and with multicolored striped indicia indicated generally at S. Numerical indicia is superimposed on the various color coded areas, where the numerical indicia is utilized to identify various pressure points on the feet of the user that will result in a reflex action to desired portions of the human body. Table A that follows identifies the numerical indicia and the part of the human anatomy that is affected by the creation of a pressure point at that region of the foot.

TABLE A

| Numerical Indicia | Effected Body Anatomy |
|---|---|
| 1 | Top of the skull |
| 2 | Eye |
| 3 | Forehead, maxillary sinus, teeth |

TABLE A-continued

| Numerical Indicia | Effected Body Anatomy |
|---|---|
| 4 | Ear, tonsils, lateral lymph channels |
| 5 | Temples, jaw |
| 6 | Cerebrum |
| 7 | Pituitary gland |
| 9 | Base of the skull |
| 10 | Neck |
| 11 | Spine, cervical region |
| 12 | Upper lymph paths |
| 13 | Thyroid, neck |
| 14 | Heart |
| 15 | Pharynx, esophagus, bronchia |
| 17 | Spine, thoracic region |
| 18 | Entrance to the stomach |
| 19 | Stomach and liver, left |
| 20 | Stomach, exit |
| 21 | Pancreas |
| 22 | Duodenum |
| 23 | Spine, lumbar region |
| 24 | Transverse colon |
| 25 | Ureter |
| 26 | Sacrum |
| 27 | Small intestine |
| 28 | Coccyx |
| 29 | Rectum, anus |
| 30 | Pelvic area |
| 31 | Pelvic area |
| 32 | Lymphatic ganglion |
| 33 | Shoulder joint |
| 35 | Lung |
| 36 | Solar plexus, diaphragm |
| 37 | Adrenal glands |
| 38 | Kidney |
| 39 | Spleen |
| 40 | Upper arm |
| 41 | Elbow |
| 42 | Lower edge of ribs. waist |
| 49 | Gallbladder |
| 64 | Appendix |
| 66 | Thymus |
| 67 | Tubes |

The undersurface of each of the reflex pin holders 14 and 16 is perforated with small apertures, such as an aperture 70. Each apertures is aligned with a corresponding one of the numerical indicia disposed on the individual plastic sheets, such as the plastic sheet 15,and is dimensioned to receive therein individual ones of the reflex pins. It should be understood by those skilled in the art that the overall thickness of the individual reflex pin holders 14, 16 is sufficiently thick to permit the distal end of each reflex pin to engage the corresponding plastic sheet at about one of its numerical indicia but not sufficiently thin to allow the reflex pin to penetrate the plastic sheet. In this manner, the reflex pin, such as the reflex pin 20 creates a desired pressure point at a precise location on the corresponding plastic sheet. Thus, for example as best seen in FIG. 5 the reflex pin 20 inserted in the hole 70 creates a pressure point N, where N corresponds to the numerical indicia point number twenty-seven as identified in Table A.

Figure 4:
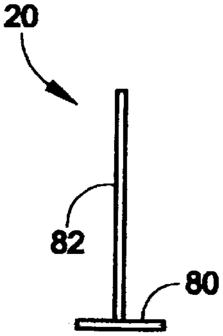
FIG. 4 is a pictorial view of a reflex pin of FIG. 1.

Considering now the reflex pin 20 in greater detail with reference to FIG. 4, the reflex pin 20 generally includes a disc like base member 80 that has a sufficient diameter to be received in a friction tight fit in the reflex pin holder, such as the aperture 70. A cylindrical post 82 extends perpendicularly upward from the disc member 80 a sufficient distance to engage an associated plastic sheet 15 as mentioned earlier. The post 82 is located at the center of the disc. From the foregoing it will be understood by those skilled in the art that the disc like base member 80 engages the undersurface of the reflex pin holder within one of the apertures and functions via its head as a stop preventing the distal end of the post 82 from extending beyond the plastic sheet.

Considering now the stress reduction method of the present invention in greater detail with reference to FIGS. 1–5, the user (not shown) removes the contents from the package 12 which include: a pair of perforated reflex pin holders consisting of a right foot reflex pin holder or right foot insole 14 and a left foot reflex pin holder or left foot insole 16, a resealable bag 18 holding a plurality 19 of similar reflex pins or pressure pins, such as the pressure pin 20, and a set of instructions 22. Utilizing the instructions 22, the user determines which part or parts of his or her body, that pressure therapy should be applied, identifying the part to be affected by a numerical reference point. The user then removes from the bag 18 a desired number of reflex pins, such as the reflex pin 20, and inserts the pins into selected ones of the apertures that are aligned with the user selected numerical indica. The user then places the pin carrying reflex pin holders into his or her shoes and steps into the shoes to permit the feet of the user to experience the various user selected pressure points. The user then begins walking allowing the reflex pins, such as the reflex pin 20 to massage the soles of the user to simulate an acupressure type massage on the soles of the feet during the walking experience.

Figure 6:
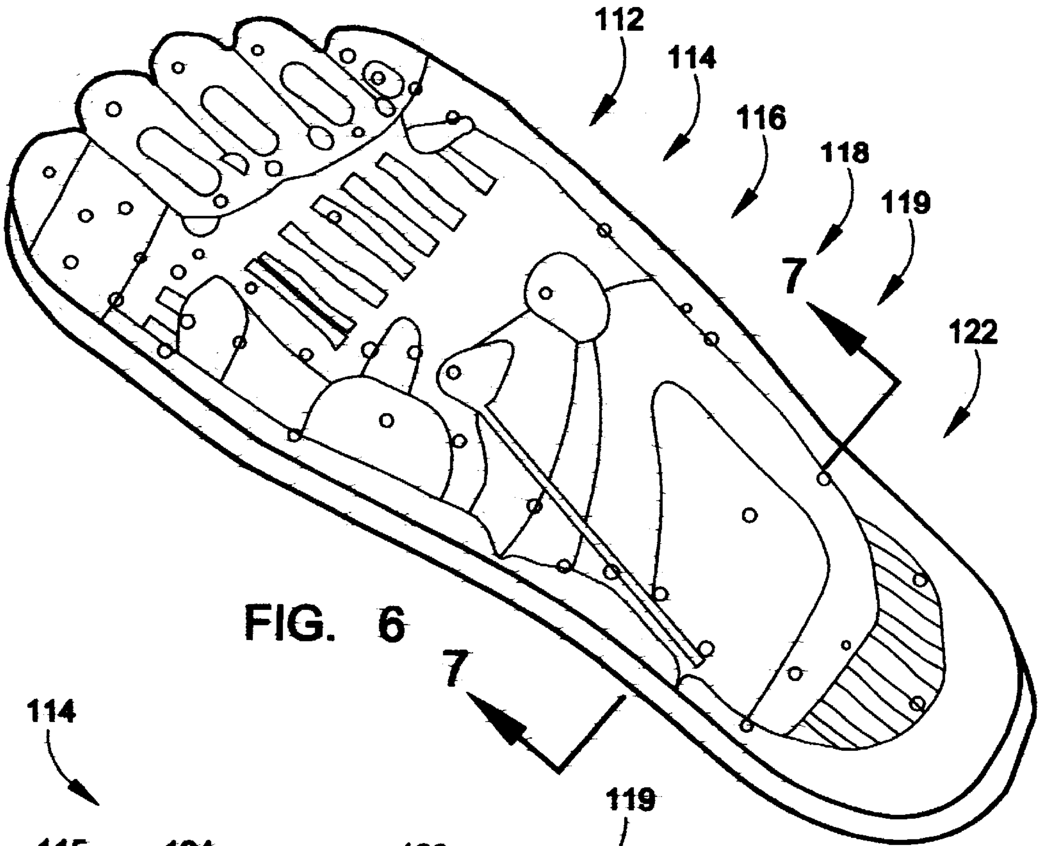
Figure 7:
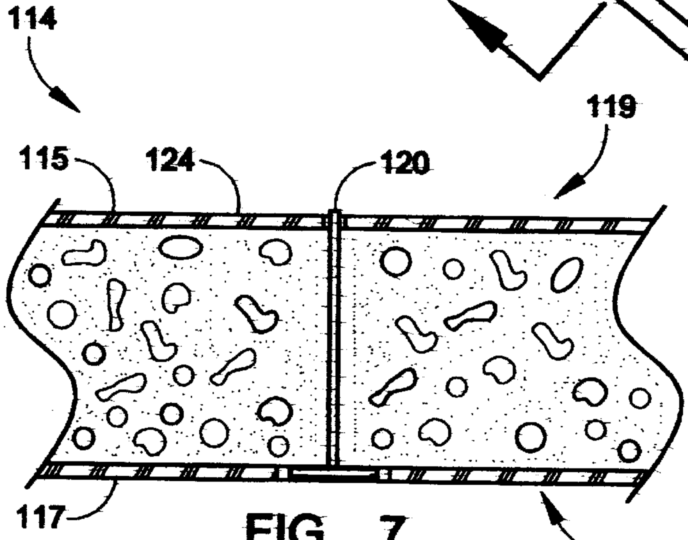
FIG. 7 is a cross sectional view taken substantially on line 7—7 of the right foot reflex pin holder of FIG. 6.

Referring now to the drawings and more particularly to FIGS. 6–7 there is illustrated another stress reduction kit 110, which is constructed in accordance with the present invention. The kit 110 generally includes a storage container 112, a pair of reflex pin holders 112 and 114, a resealable bag 118 holding a plurality or reflex pins, such as a reflex pins 120 (FIG. 7), and a set of instructions 122. The kit 110 is substantially identical to kit 10 with the exception of its reflex pin holders 112 and 114. In this regard, only the reflex pin holder 114 will be described hereinafter in greater detail.

Considering now the reflex pin holder 114 in greater detail with reference to FIGS. 1 and 7, the reflex pin holder 114 is composed of a sponge like cellular material, such as a latex foam material 124, with a consistency ranging from flexible to substantially ridged with a high degree of resilience. The holder 114 is shaped to conform to the shape of the under portion of the anatomy of a human foot so as to function as an inner sole for the shoe of a user. In this regard, the holder may be dimensioned to fit within shoes of various sizes and widths.

The reflex pin holder 114 is substantially identical in construction to holder 14 except the block of foam material 124 is sandwiched between a pair of perforated plastic sheets 115 and 117 respectively. Each of the perforated plastic sheets 115 and 117 carry an identical reflexology chart, such as a reflexology chart 119. The reflexology chart 119 is substantially similar to reflexology chart 17 and will not be described hereinafter in greater detail.

Considering now the reflex pin 120 in greater detail with reference to FIG. 7, the reflex pin 120 is substantially identical to reflex pin 20 except that its overall length is slightly longer. In this regard, the reflex pin 120 is sufficiently long so that it extends slightly above the upper surface of the plastic sheet 115 when the pin 120 is supported within the reflex pin holder 114. In this manner a more direct pressure point is formed against the foot of a user when the user applies bodily pressure against the pin carrying reflex pin holder 112.

Although in the preferred embodiment of the present invention the reflexology chart 119 has been described as being carried by the plastic sheets 115 and 117 respectively, it is contemplated within the scope of the present invention, that the chart 119 may be printed directly on the top and bottom surfaces of the block of the material 124. In this regard, the plastic sheets 115 and 117 then act as protectors for the indicia disposed on the top and bottom surfaces of the material 124.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A stress reduction kit, comprising:

at least one insole;

said insole including:

a pair of foot reflexology charts, each individual chart being shaped to conform to the under portion of the anatomy of a human foot and wherein at least one of said pair of foot reflexology charts is perforated with a plurality of apertures arranged in a predetermined pattern corresponding to a plurality of reflex areas associated with said foot reflexology chart;

a sheet of foam material sandwiched between said pair of foot reflexology charts, said sheet having a top surface and a bottom surface and having a shape conforming to the under portion of the anatomy of a human foot;

said sheet being perforated with a plurality of apertures arranged in a predetermined pattern corresponding to said plurality of reflex areas associated with said foot reflexology chart;

wherein each individual one of said plurality of apertures disposed in said sheet of foam material has a diameter dimensioned for receiving therein a reflex pin for providing a pressure point at an individual one of said plurality of reflex areas associated with the foot reflexology chart; and wherein said sheet is sufficiently thick to permit said reflex pin to provide said pressure point at an individual one of said plurality of reflex areas associated with the foot reflexology chart, but not sufficiently thin to permit said reflex pin to penetrate said reflexology chart.

2. A stress reduction kit according to claim 1, wherein said reflex pin is a metallic T-shaped pin.

3. An insole, comprising:

a pair of foot reflexology charts, each individual chart being shaped to conform to the under portion of the anatomy of a human foot and wherein at least one of said pair of foot reflexology charts is perforated with a plurality of apertures arranged in a predetermined pattern corresponding to a plurality of reflex areas associated with said foot reflexology chart;

a sheet of foam material sandwiched between said pair of foot reflexology charts, said sheet having a top surface and a bottom surface and having a shape conforming to the under portion of the anatomy of a human foot;

said sheet being perforated with a plurality of apertures arranged in a predetermined pattern corresponding to said plurality of reflex areas associated with said foot reflexology chart;

wherein each individual one of said plurality of apertures disposed in said sheet of foam material has a diameter dimensioned for receiving therein a reflex pin for providing a pressure point at an individual one of said plurality of reflex areas associated with the foot reflexology chart; and wherein said sheet is sufficiently thick to permit said reflex pin to engage an individual one of said reflexology charts at about the top surface of said sheet for providing said pressure point, but not sufficiently thin to permit said reflex pin to penetrate said reflexology chart disposed at about the top surface of said sheet.

4. A stress reduction kit, comprising:

a sheet of material sandwiched between a pair of foot reflexology charts;

said sheet having a plurality of perforations arranged in a predetermined pattern corresponding to a plurality of reflex areas associated with each individual one of said pair of reflexology charts; and said sheet having an insufficient thickness to permit a reflex pin to pass therethrough but not such an insufficient thickness to permit a reflex pin to be received therein for providing a pressure point at an individual one of reflex areas.

5. The stress reduction kit according to claim 4, wherein said reflex areas are distinguishable, one group from another, by their respective color indicia.

6. The stress reduction kit according to claim 4, wherein said sheet of material is an insole.

7. The stress reduction kit according to claim 4, further comprising:

a container for holding said sheet.

8. The stress reduction kit according to claim 4, wherein said reflex pin is metallic.

9. The stress reduction kit according to claim 8, wherein said reflex pin is T-shaped.

10. The stress reduction kit according to claim 7, further comprising:

a set of instructions for using the kit to reduce stress.

11. A stress reduction kit, comprising:

a container for facilitating displaying the stress reduction kit;

a pair of reflex pin holders wherein each reflex pin holder is sandwiched between a pair of flexible plastic sheets and is dimensioned to be received within an interior portion of said container;

right foot color coded indicia disposed on one of said pair of flexible plastic sheets for defining a pair of identical reflexology charts;

left foot color coded indicia disposed on another one of said pair of flexible plastic sheets for defining another pair of identical reflexology charts right foot numerical indicia disposed on said right foot color coded indicia for identifying a set of pressure point areas affecting desired areas of the body, wherein at least one of said plastic sheets has a plurality of apertures, each aperture being disposed at about an individual one of said right foot numerical indicia;

left foot numerical indicia disposed on said left foot color coded indicia for identifying another set of pressure point areas affecting desired areas of the body, wherein at least one of said plastic sheets has a plurality of apertures, each aperture being disposed at about an individual one of said left foot numerical indicia;

a plurality of reflex pins, each pin being dimensioned to be received in an individual one of said plurality of apertures in a snug friction tight fit and each pin having a stop for limiting the penetration of the pin within said aperture;

a resealable bag for holding said plurality of reflex pins within said interior portion of said container; and a set of instruction for identifying which ones of said right foot numerical indica and which ones of said left foot numerical indicia correspond to desired areas of the body.

12. A stress reduction kit according to claim 11, wherein the right foot indicia and the left foot indicia is arranged in a plurality of reflex areas associated with specific body parts in the human body, each reflex area having disposed therein an aperture for receiving therein said at least one reflex pin.

13. A stress reduction kit according to claim 12, wherein said reflex areas are distinguishable, one group from another, by their respective color indicia.

14. A stress reduction kit according to claim 13, wherein the respective color indicia include:

a red color indicia;

a green color indicia;

a blue color indicia;

a yellow color indicia; and a multi-colored indicia;

wherein said red color indicia, said green color indicia, said blue color indicia, said yellow color indicia and said multi-colored indicia are arranged on a top face portion of said reflex pin holder to help identify a plurality of body parts within the body of the user.

15. A stress reduction kit according to claim 14, further comprising:

at least one carrier for holding at least one of said reflex pin holders in a substantially stationary position relative to a specific body part of the user.

16. A stress reduction kit according to claim 15, wherein said at least one carrier is a shoe.

17. A stress reduction kit according to claim 11, wherein said at least one reflex pin holder is an insole with a plurality of perforations, said perforations each being dimensioned to receive therein said at least one reflex pin.

18. A stress reduction kit according to claim 11, wherein said instructions further direct the user in assembling the stress reduction kit to achieve one of its intended purpose of strengthening the body immune system of a user.

19. A stress reduction kit according to claim 11, further comprising:

at least one carrier for helping to position said at least one reflex pin holder and said at least one reflex pin in a desired body position of the user, whereby when said user creates body pressure on said carrier, said reflex pin creates said user desired pressure point on the body of the user.

20. A stress reduction kit according to claim 19, wherein said at least one reflex pen is a metallic T-shaped pin for applying pressure to a desired pressure point on the foot of a user.

21. A stress reduction kit according to claim 11, wherein said container further helps to display the stress reduction kit for sale purposes and to contain said reflex pin holders, said reflex pins and said set of instructions in close proximity to one another to facilitate ease of use.

22. A stress reduction kit according to claim 11, wherein said container is a pyramid shaped display box.

23. A stress reduction kit according to claim 11, wherein said container is a plastic bag.

24. A stress reduction kit according to claim 11, wherein said container is an irregular shaped box.

25. A stress reduction kit according to claim 24, wherein said irregular shaped box has a pyramid shape.

26. A stress reduction kit according to claim 11, wherein each of said plurality of reflex pins is metallic.

27. A stress reduction kit according to claim 11, wherein each of said plurality of reflex pins are composed of a plastic material.

28. A stress reduction kit according to claim 11, wherein another one of said pair of flexible plastic sheets has another plurality of apertures, each aperture being disposed at about an individual one of said left foot numerical indicia; and wherein yet another one of said pair of flexible plastic sheets has yet another plurality of apertures, each aperture being disposed at about an individual one of said right foot numerical indicia;

whereby individual ones of said plurality of reflex pins when received within an individual one of said reflex pin holders completely penetrates the pair of flexible plastic sheets sandwiching said reflex pin holder to help facilitate providing a direct pressure point against the foot of a user.

* * * * *